(12) United States Patent
Barendse et al.

(10) Patent No.: US 6,500,426 B1
(45) Date of Patent: Dec. 31, 2002

(54) CARBOHYDRATE-BASED ENZYME-CONTAINING GRANULES FOR USE IN ANIMAL FEED

(76) Inventors: Rudolf Carolus Maria Barendse, Van Bossestraat 9, 2613 CM Delft (NL); Gabriel Marinus Henricus Meesters, Hof van Saffier 9, 2614 TJ Delft (NL); Hans-Peter Harz, Am Mönschbusch 22, D-67373 Dudenhofen (DE)

( * ) Notice: Subject to any disclaimer, the term of this patent is extended or adjusted under 35 U.S.C. 154(b) by 0 days.

(21) Appl. No.: 09/090,528

(22) Filed: Jun. 4, 1998

Related U.S. Application Data
(60) Provisional application No. 60/048,611, filed on Jun. 4, 1997, now abandoned.

(30) Foreign Application Priority Data
Jun. 4, 1997  (EP) .............................................. 97201641

(51) Int. Cl.[7] ........................ A61K 38/43; A61K 38/46; C12N 11/10; C12N 9/98; C12N 9/96
(52) U.S. Cl. .................... 424/94.1; 424/94.3; 424/94.6; 424/94.61; 426/2; 426/805; 426/807; 435/177; 435/178; 435/179; 435/187; 435/188
(58) Field of Search ................................. 435/174, 177, 435/178, 179, 180, 182; 424/94.1, 94.3, 94.6, 94.61; 426/2, 805, 807

(56) References Cited

U.S. PATENT DOCUMENTS

| | | | |
|---|---|---|---|
| 3,661,786 A | 5/1972 | Desforges et al. | 252/99 |
| 4,106,991 A | 8/1978 | Markussen et al. | 435/187 |
| 4,740,469 A | 4/1988 | Nishinaka et al. | 435/187 |
| 4,959,240 A | 9/1990 | Aulik et al. | 426/637 |
| 4,988,520 A | 1/1991 | Overton | 426/74 |
| 5,010,008 A | 4/1991 | Brumm et al. | 435/202 |
| 5,397,834 A | 3/1995 | Jane et al. | 525/54.1 |
| 5,612,055 A | 3/1997 | Bedford et al. | 424/442 |
| 5,972,668 A | * 10/1999 | Georg et al. | 435/188 |

FOREIGN PATENT DOCUMENTS

| | | |
|---|---|---|
| DE | 33 44 104 | 12/1983 |
| EP | 0 168 526 | 1/1986 |
| EP | 0 257 996 | 3/1988 |
| EP | 0 304 332 | 2/1989 |
| EP | 0 420 358 | 4/1991 |
| EP | 0 569 468 | 11/1993 |
| EP | 0 684 313 | 11/1995 |
| EP | 0 758 018 | 2/1997 |
| GB | 2 225 784 | 11/1989 |
| WO | WO92/12645 | 8/1992 |
| WO | WO93/14645 | 8/1993 |
| WO | WO 94/03612 | 2/1994 |
| WO | WO 94/26883 | 11/1994 |
| WO | WO95/28850 | 11/1995 |
| WO | WO 97/16076 | 5/1997 |
| WO | WO 97/39116 | 10/1997 |

OTHER PUBLICATIONS

Stroucken et al., "Extruding vs Pelleting of a Feed Mixture Lowers Apparent Nitrogen Digestibility in Dogs", *J. Sci. Food Agric.*, 71, 520–522 (1996).

* cited by examiner

*Primary Examiner*—David M. Naff
(74) *Attorney, Agent, or Firm*—McDonnell, Boehnen, Hulbert & Berghoff

(57) ABSTRACT

Enzyme-containing granules for manufacturing animal feed compositions are prepared using a carrier containing at least about 15% (w/w) carbohydrate such as starch and less than 5% (w/w) protein. A mixture is formed containing an enzyme, the carrier and water, with or without prior kneading to improve plasticity, the mixture is mechanically processed such as by extrusion with a basket or dome extruder while not allowing the temperature of the mixture to rise above about 40° C., and drying the resultant enzyme-containing granules. The granules may be spheronised prior to drying, and drying may be in a fluid bed agglomerator. The water and enzyme may be provided as an enzyme-containing aqueous liquid such as an enzyme-containing filtrate from a fermentation process. Enzymes include phytase, endo-xylanase and β-glucanase. Other components that may be in the granules include divalent cations, cellulose, polyvinyl alcohol and an edible oil. Animal feed compositions may be prepared by mixing the granules with feed ingredients, sterilizing or treating with steam, and pelleting. The compositions show improved enzyme stability during pelleting.

23 Claims, No Drawings

CARBOHYDRATE-BASED ENZYME-CONTAINING GRANULES FOR USE IN ANIMAL FEED

CROSS REFERENCE TO RELATED APPLICATIONS

This application claims the priority of U.S. Provisional Patent Application 60/048,611 filed Jun. 4, 1997, now abandoned, and European Patent Application No. 97201641.4 filed in the Netherlands on Jun. 4, 1997. These applications hereby are incorporated in their entireties by reference.

FILED OF THE INVENTION

The present invention relates to the formulation of enzymes, preferably feed-enzymes, into carbohydrate (e.g., starch-) containing granulates, and to processes for the preparation of such enzyme-containing granulates. These (edible) granulates can then be used in animal feeds.

BACKGROUND OF THE INVENTION

The use of various enzymes in animal, e.g., livestock, feed has become almost common practice. These enzymes are usually produced by culturing microorganisms in large-scale fermenters operated by industrial enzyme producers. At the end of the fermentation the resulting "broth" is usually subjected to a series of filtration steps to separate the biomass (the microorganisms) from the desired enzyme (in solution). The enzyme solution is either then sold as a liquid (often after addition of various stabilizers) or processed to a dry formulation.

Enzyme liquid and dry formulations are used on a commercial scale by the feed industry. Liquid formulations may be added to the feed after pelleting in order to avoid heat inactivation of the enzyme(s) which would occur during the pelleting process. However the amounts of enzyme in the final feed preparations are usually very small which makes it difficult to achieve a homogenous distribution of the enzyme in the feed, and liquids are notoriously more difficult to mix evenly than dry ingredients. In addition one needs specialised (expensive) equipment to add liquids to the feed after pelleting which is not currently available at most feed mills (due to the extra cost).

Dry formulations of enzyme(s), on the other hand, have the disadvantage of heat-inactivation of the enzymes during pelleting. Preferred manufacturing protocols in the feed industry involve steam pelleting where the feed is subjected to steam injection(s) prior to pelleting. In the subsequent pelleting step the feed is forced through a matrix or die and the resulting strips are cut into suitable pellets of variable length. The moisture content immediately before pelleting is generally between 18% and 19%. During this process temperatures may rise to 60–95° C. The combined effect of high moisture content and high temperature is detrimental to most enzymes. These disadvantages are also encountered in other types of thermomechanical treatments such as extrusion and expansion.

In order to try and overcome these problems EP-A-0,257, 996 (Cultor Ltd.) suggests that the stability of enzymes in feed processing could be increased by the preparation of an enzyme "premix" where an enzyme-containing solution is absorbed onto a grain-based carrier consisting of flour, and the premix is subsequently pelleted and dried. However, these flour-based premixes are not suitable for gentler methods of processing (of the dough-like premix) into granulates, such as low-pressure extrusion or high shear granulation, because of the gluey character of the flour-based premixes.

Various enzyme manufacturers have developed alternative formulation methods to try to improve the stability of dry enzyme products during pelleting and storage.

EP-A-0,569,468 (Novo Nordisk) refers to a formulation consisting of a enzyme-containing "T-granulate" that is coated with a high melting wax or fat alleged to improve resistance to pelleting conditions. The granulate is prepared by mixing a dry inorganic (e.g., sodium sulphate) filler with the enzyme solution in a high shear granulator. EP-A-0,569, 468 teaches that any beneficial effect of the coating with respect to pelleting stability is specific for the type of granulate coated, which in this case is based on a sodium sulphate filler. However, the absorption capacity of these (sodium sulphate) fillers is much less than that of carriers such as flour, which is undesirable if one wishes to produce more concentrated enzyme-containing granulates.

In addition, the granulates have a wide particle size distribution which makes it difficult to obtain a homogeneous enzyme concentration throughout. Moreover the bioavailability of the enzyme to the animal is decreased by the wax or fat coating.

WO-A-97/16076 (Novo Nordisk) also refers to the use of waxes and other water-insoluble substances in particulates, but here they are employed as a matrix material.

There is thus a need for stable formulations of enzymes that are based on a carrier that is suitable for granulation methods other than pelleting and that can have a high absorption capacity. Further objects and advantages of the invention will be apparent from the description herein.

BRIEF SUMMARY OF THE INVENTION

The present invention provides carbohydrate-based enzyme granulates and methods for the preparation of same. The granulates can be employed inter alia in animal feed compositions.

DETAILED DESCRIPTION OF THE INVENTION

In a first preferred aspect of the present invention there is provided a process for the preparation of an enzyme-containing granulate suitable for use in an animal feed, the process preferably comprising processing an enzyme, a solid carrier comprising at least about 15% (w/w) of an edible carbohydrate polymer, and water in appropriate relative amounts to obtain enzyme-containing granules, and subsequently drying the granules. The enzyme-containing granulate produceable by this process (which forms the second preferred aspect of the invention that preferably covers a granulate comprising dried granules formed from an enzyme and a solid carrier which comprises at least about 15% (w/w) of an edible carbohydrate polymer) seeks to solve or at least mitigates the problems encountered in the prior art.

The invention can thus preferably provide processes for the preparation of enzyme formulations in the form of granulates that use the carbohydrate as a carrier. The carrier desirably can be in particulate or powder form. The enzyme and water are preferably provided as an enzyme-containing (preferably aqueous) liquid, such as a solution or a slurry, which can be mixed with the solid carrier and allowed to absorb onto the carrier. During or after the mixing, the enzyme-containing liquid and the carrier are processed into a granulate, which optionally can then subsequently be dried. The use of the carbohydrate carrier can allow the absorption of large amounts of enzyme-containing liquid (and therefore enzyme). The mixture desirably can be used to form a plastic paste or non-elastic dough that can readily be processed into granules, for example it is extrudable. Suitably the carrier is non-fibrous which allows for easier granulation: fibrous materials can prevent granulation by extrusion.

A number of prior art documents refer to pellets containing various enzymes, but these find use as detergents, often in washing compositions. In contrast, the present invention finds use in animal feeds and, for that reason, the granulates of the invention are edible (by animals) and preferably also digestible. It therefore is a surprising and unexpected aspect of the present invention that the granulates, granules and compositions of the invention are free of soap, detergents and bleach or bleaching compounds, zeolites, binders, fillers ($TiO_2$, kaolin, silicates, talc, etc.) to name but a few.

The edible carbohydrate polymer should be chosen so that it is edible by the animal for whom the feed is intended, and preferably is digestible as well. The polymer preferably comprises glucose (e.g., a glucose-containing polymer), or $(C_6H_{10}5)_n$, units. Preferably the carbohydrate polymer comprises α-D-glucopyranose units, amylose (a linear (1→4) α-D-glucan polymer) and/or amylopectin (a branched D-glucan with α-D-(1→4) and α-D-(1→6) linkages). Starch is the preferred carbohydrate polymer. Other suitable glucose-containing polymers that can be used instead of, or in addition to starch, include α-glucans, β-glucans, pectin (such as proto-pectin), and glycogen. Derivatives of these carbohydrate polymers, such as ethers and/or esters thereof, are also contemplated although gelatinised starch is best avoided and thus may not be present. Suitably the carbohydrate polymer is water-insoluble.

In the examples described herein corn-, potato- and rice-starch is used. However, starch obtained from other (e.g., plant, such as vegetable or crop) sources such as tapioca, cassava, wheat, maize, sago, rye, oat, barley, yam, sorghum, or arrowroot is equally applicable. Similarly both native or modified (e.g., dextrin) types of starch can be used in the invention. Preferably the carbohydrate (e.g., starch) contains little or no protein, e.g., less than about 5% (w/w), such as less than about 2% (w/w), preferably less than about 1% (w/w). Even more desirably, the carbohydrate contains from about 0.005% (w/w) to about 1% (w/w). Regardless of the type of starch (or other carbohydrate polymer) it should be in a form that allows it to be used in an animal feed, in other words an edible or digestible form.

At least about 15% (w/w) of the solid carrier desirably can comprise the carbohydrate polymer (such as starch). Preferably, however, at least about 30% (w/w) of the solid carrier comprises the carbohydrate, optimally at least about 40% (w/w). Advantageously the major component of the solid carrier is the carbohydrate (e.g., starch), for example more than about 50% (w/w), preferably at least about 60% (w/w), suitably.: at least about 70% (w/w), and optimally at least about 80% (w/w). Thus, desirably the carbohydrate comprises from about 40% to about 100% (w/w), particularly from about 70% to about 90% (w/w) of the solid carrier. These weight percentages are based on the total weight of the non-enzymatic components in the final dry granulate.

In the process of the invention the enzyme and water can be present in the same composition before contacting the solid carrier. In this respect, one preferably can provide an enzyme-containing aqueous liquid. This liquid preferably can be a solution or a slurry that is from, or derived from, a fermentation process. This fermentation process will usually be one in which the enzyme is produced. The fermentation process desirably can result in a broth which contains the microorganisms (which produce the desired enzyme) and an aqueous solution. This aqueous solution, once separated from the microorganisms (for example, by filtration) desirably can be the enzyme-containing aqueous liquid used in the invention. Thus, in preferred embodiments the enzyme-containing aqueous liquid is a filtrate.

The amount of enzyme-containing liquid (and so enzyme) that can be absorbed onto the carrier is usually limited by the amount of water that can be absorbed. For natural, granular, starch this can vary between from about 25% (w/w) to about 30% (w/w), without using elevated temperatures (that cause the starch to swell). In practice the percentage of enzyme liquid to be added to the carbohydrate will often be much larger than this because the enzyme containing liquid will usually contain a significant amount of solids. The enzyme solution can contain about 25% (w/w) solids (optimally from about 15% to about 40% (w/w)), as a result of which the carbohydrate (e.g., starch) and enzyme solution can be mixed at a ratio of carbohydrate:enzyme solution of from about 0.5:1 to about 2:1, e.g., from about 1.2:1 to about 1.6:1, such as at a ratio of about 60% (w/w):40% (w/w), respectively. Preferably the amount of liquid added to the solid carrier is such that (substantially) all the water in the (aqueous) liquid is absorbed by the carbohydrate present in the solid carrier.

At elevated temperatures starch and other carbohydrate polymers can absorb much larger amounts of water under swelling. For this reason the carbohydrate polymer is desirably able to absorb water (or enzyme-containing aqueous liquids). For example, corn starch can absorb up to three times its weight of water at 60° C. and up to ten times at 70° C. The use of higher temperatures in order to absorb a greater amount enzyme-containing liquid is thus contemplated by the present invention, and indeed is preferable especially when dealing with thermostable enzymes. For these enzymes therefore the mixing of the solid carrier and liquid (or enzyme and water) can be conducted at elevated temperatures (e.g., above ambient temperature), such as above about 30° C., preferably above about 40° C., and optimally above about 50° C. In particular, depending on the thermostability of the enzymes employed, desirably mixing can be done at temperatures from about 30° C. to about 80° C. Alternatively or in addition, the liquid can be provided at this temperature.

However, in general, non-swelling conditions at lower (e.g., ambient) temperatures are preferred. This can minimise activity loss arising from instability of (heat sensitive) enzymes at higher temperatures. Suitably the temperature during the mixing of the enzyme and water is from about 20° C. to about 35° C., and more preferably at from about 20° C. to about 25° C.

The mechanical processing used in the present invention for making the mixture of the enzyme, water (e.g., an enzyme-containing liquid) and the solid carrier into granules (in other words granulating) can employ known techniques frequently used in food, feed and enzyme formulation processes. This can comprise expansion, extrusion, spheronisation, pelleting, high shear granulation, drum granulation, fluid bed agglomeration or a combination thereof. These processes are usually characterised by an input of mechanical energy, such as the drive of a screw, the rotation of a mixing mechanism, the pressure of a rolling mechanism of a pelleting apparatus, the movement of particles by a rotating bottom plate of a fluid bed agglomerator or the movement of the particles by a gas stream, or a combination thereof. These processes allow the solid carrier (e.g., in the form of a powder), to be mixed with the enzyme and water, for example an enzyme-containing liquid (an aqueous solution or slurry), and so subsequently granulated.

Alternatively the solid carrier desirably can be mixed with the enzyme (e.g., in a powder form) to which water, such as a liquid (or slurry) is then added (which can act as granulating liquid).

In yet a further preferred embodiment of the invention the granulate (e.g., an agglomerate) is formed by spraying or coating the enzyme-containing liquid onto the carrier, such as in a fluid bed agglomerator. Here the resulting granules can include an agglomerate as can be produced in a fluid bed agglomerator.

Preferably the mixing of the enzyme-containing liquid and the solid carrier additionally comprises kneading of the mixture. This can improve the plasticity of the mixture in order to facilitate granulation (e.g., extrusion).

If the granulate is formed by extrusion this is preferably performed at low pressure. This can offer the advantage that the temperature of the mixture being extruded will not increase, or increases only slightly. Low-pressure extrusion includes; extrusion for example in a Fuji Paudal basket- or dome- extruder. Preferably extrusion does not result in the temperature of the material being extruded to rise above about 40° C. The extrusion can naturally produce granules (the granules can break off after passage through a die) or a cutter can be employed.

Suitably the granules will have a water content of from about 30% to about 40%, such as from about 33% to about 37%. The enzyme content is preferably from about 3% to about 15%, such as from about 5% to about 12% (e.g., at least about 50,000 ppm).

The granules obtained desirably can be subjected to rounding off (e.g., spheronisation), such as in a spheromiser, .e.g., a MARUMERISER™ machine and/or compaction. The granules preferably can be spheronised prior to drying since this can reduce dust formation in the final granulate and/or can facilitate any coating of the granulate.

The granules preferably can then be dried, such as in a fluid bed drier or, in case of the fluid bed agglomeration, desirably can be immediately dried (in the agglomerator) to obtain (solid dry) granulates. Other known methods for drying granules in the food, feed or enzyme industry can be used by the skilled person. Suitably the granulate is flowable.

The drying preferably takes place at a temperature of from about 25° C. to about 60° C., such as from about 30° C. to about 50° C. Here the drying can last from about 10 minutes to about several hours, such as from about 15 minutes to about 10 hours, preferably from about 15 minutes to about 3 hours, or desirably from about 15 minutes to about 30 minutes. The length of time required will of course depend on the amount of granules to be dried, but as a guide this is from about 1 to about 2 seconds per kg of granules.

After drying the granules, the resulting granulate preferably has a water content of from about 3% to about 10%, such as from about 5% to about 9%.

A coating preferably can be applied to the granulate to give additional (e.g., flavoured) characteristics or properties, like low dust content, colour, protection of the enzyme from the surrounding environment, different enzyme activities in one granulate, or a combination thereof. The granules can be coated with a fat, wax, polymer, salt, unguent and/or ointment or a coating (e.g., liquid) containing a (second) enzyme or a combination thereof. It will be apparent that if desired several layers of (different) coatings can be applied. To apply the coating(s) onto the granulates a number of known methods are available which include the use of a fluidised bed, a high shear granulator, a mixer granulator, or a Nauta-mixer.

In other embodiments additional ingredients can be incorporated into the granulate where desirable, e.g., as processing aids, for further improvement of the pelleting stability and/or the storage stability of the granulate. A number of such preferred additives are discussed below.

Salts preferably can be included in the granulate, (e.g., with the solid carrier or water). Preferably (as suggested in EP-A-0,758,018) inorganic salt(s) can be added, which can improve the processing and storage stability of the dry enzyme preparation. Preferred inorganic salts are water soluble. They can comprise a divalent cation, such as zinc (in particular), magnesium, and calcium. Sulphate is the most favoured anion although other anions resulting in water solubility can be used. The salts optionally can be added (e.g., to the mixture) in solid form. However, the salt(s) also desirably can be dissolved in the water or enzyme-containing liquid prior to mixing with the solid carrier. Suitably the salt is provided at an amount that is at least about 15% (w/w based on the enzyme), such as at least about 30%. However, it can be as high as at least about 60%, or even about 70%, for a maximum range of from about 15% to about 70% (again, w/w based on the enzyme). These amounts can apply either to the granules or to the granulate. The granulate therefore can comprise less than about 12% (w/w) of the salt, for example from about 2.5% to about 7.5% (w/w), e.g., from about 4% to about 6% (w/w).

If the salt is provided in the water then it can be in an amount of from about 5% to about 30% (w/w), such as from about 15% to about 25% (w/w).

Further improvement of the pelleting stability can be obtained where desirable by the incorporation of hydrophobic, gel-forming-or-slow dissolving (e.g., in water) compounds. These can be provided at from about 1% to about 10%, such as from about 2% to about 8%, and preferably from about 4% to about 6% by weight (based on the weight of water and solid carrier ingredients). Suitable substances include but are not limited to derivatised celluloses, such as HPMC (hydroxy-propyl-methyl-cellulose), CMC (carboxy-methyl-cellulose), HEC (hydroxy-ethyl-cellulose); polyvinyl alcohols (PVA); and/or edible oils. Edible oils, such as soy oil or canola oil or other appropriate oil, can be added (e.g., to the mixture to be granulated) as a processing aid, although often it will be preferred that the granulate does not contain any hydrophobic substances (e.g., palm oil).

Preferably the granules have a relatively narrow size distribution (e.g., they are monodisperse). This can facilitate a homogeneous distribution of the enzyme in the granules and/or the enzyme granulate in the animal feed. The process of the invention tends to produce granulates with a narrow size distribution. However, if necessary, an additional step can be included in the process to further narrow the size distribution of the granules, such as screening. The size distribution of the granulate is suitably between about 100 $\mu$m and about 2000 $\mu$m, preferably between about 200 $\mu$m and 25 about 800 $\mu$m, and optimally between about 300 $\mu$m and about 1600 $\mu$m. The granules can be of irregular (but preferably are regular) shape, for example, approximately spherical.

The water or enzyme-containing liquid can comprise one or more enzyme(s) and are usually of microbial origin, e.g., obtained from a microbial fermentation. Usually the enzyme will be in an active form (for example it may have catalytic or physiological activity). Preferably the liquid is in a concentrated form, such as an ultra-filtrate (UF), which can allow the production of a granulate with a desired activity level.

Suitable enzyme(s) are those to be included in animal feed which includes pet food. The function of these enzymes is often to improve the feed conversion rate, e.g., by reducing the viscosity or by reducing the anti-nutritional effect of certain feed compounds. Feed enzymes (such as phytase) can also be used, such as to reduce the amount of compounds which are harmful to the environment in the manure. Preferred enzymes for these purposes include but are not limited to: phosphatases, such as phytases (both 3-phytases and 6-phytases) and/or acid phosphatases; carbohydrases, such as amylolytic enzymes and plant cell wall degrading enzymes of which include cellulases such as β-glucanases, hemicelluloses such as xylanases, or galactanases; peptidases, galactosidases, pectinases, esterases; proteases, preferably with a neutral and/or acidic pH optimum; and lipases, preferably phospholipases such as the mammalian pancreatic phospholipases A2.

Preferably, the enzyme does not include starch degrading enzymes (for example amylases). In some embodiments proteases desirably can be excluded as these may cause harm if ingested.

If the enzyme is a phosphatase, such as a phytase, then preferably the final granulate can have an activity of from about 5,000 to about 10,000 such as from about 6,000 to about 8,000, FTU/g. If the enzyme is a plant cell wall degrading enzyme, for example a cellulose, and in particular a hemicellulose such as xylanase, then the final granulate preferably can have an activity of the enzyme ranging from about 3,000 to about 100,000, preferably from about 5,000 to about 80,000, and optimally from about 8,000 to about 70,000, EXU/g. If the enzyme is a cellulose, such as β-gluconase, then the final granulate desirably can have an enzyme activity of from about 500 to about 15,000, preferably from about 1,000 to about 10,000, and optimally from about 1,500 to about 7,000, BGU/g.

One FTU(phytase unit) is the amount of enzyme which liberates 1 micromole of inorganic phosphorus per minute from 0.0051 Mol/L of sodium-phytate at pH 5.5 and 37° C. FTU can be calculated using any standard means, and, desirably, using the method of Engelen et al., *Journal of AOAC International*, 77 (3), 760–764 ("Simple and Rapid Determination of Phytase Activity"). One EXU (endoxylanase unit) is the amount of enzyme which liberates 1 micromole of reducing sugars (measured as xylose equivalents) per minute from a 1% xylan solution at pH 3.5 and 40° C. One BGU (Betaglucanase unit) is the amount of enzyme which liberates 0.278 micromole reducing sugars (measured as glucose equivalents) per minute at pH 3.5 and 40° C. at a substrate concentration of 0.5% betaglucan from barley. EXU and BGU can be calculated using any standard means, and desirably, using the method of Engelen et al., *Journal of AOAC International*, 79 (5); "Viscosimetric determination of β-glucanase and endoxylanase activity in feed" (1996). Even more preferably, FTU, EXU, and BGU are measured and determined as described in the Examples which follow ("General Materials and Methods").

The granules desirably can comprise from about 5% to about 20%, e.g., from about 7% to about 15% of the enzyme(s). The enzyme can be naturally occurring or recombinant (i.e., including synthetic).

In addition to these enzymes the invention is equally applicable to polypeptides with other biological activities, such as antigenic determinants, for example, that find use in vaccines and/or polypeptides engineered to have an increased content of essential amino acids, of which the biological activity may be sensitive to thermal inactivation, and the term "enzyme" as used herein is to be construed accordingly.

A preferred process according to the invention therefore comprises:

a. mixing the water, enzyme and solid carrier comprising at least about 15% (w/w) or an edible carbohydrate polymer, for example mixing the solid carrier with an aqueous enzyme-containing liquid;

b. optionally kneading the resulting mixture;

c. granulating, for example by mechanical processing, the mixture in order to obtain enzyme-containing granules, for example by using a granulator or by extrusion;

d. optionally spheronising the granules;

e. drying the resultant granules to obtain an enzyme-containing granulate.

During the entire process one desirably will aim to keep the maximum temperature to which the enzyme(s) are exposed to below about 80° C. In particular, preferably mixing can be done at temperatures of from about 30° C. to about 800° C., and drying can be done at temperatures of from about 25° C. to about 60° C.

The granulates of the invention are suitable for use in the preparation of an animal feed. In such processes, the granulates desirably are mixed with feed substances, either as such, or as part of a premix. The characteristics of the granulates according to the invention allows their use as a component of a mixture which is well suited as an animal feed, especially if the mixture is steam treated and subsequently pelleted. The dried granules desirably can be visible or distinguishable in such pellets.

Thus a third preferred aspect of the present invention relates to a process for the preparation of animal feed, or a premix or precursor to an animal feed, the process preferably comprising mixing a granulate of the second aspect with one or more animal feed substances (e.g., seeds) or ingredients. This desirably can then be sterilised, e.g., subjected to heat treatment. The resulting composition is then suitably processed into pellets.

A fourth preferred aspect of the invention relates to a composition comprising a granulate of the second preferred aspect, which composition is preferably an edible feed composition such as an animal feed. This composition is preferably in the form of pellets (there can be from about 1 to about 5, e.g., from about 2 to about 4, dried granules per pellet).

The composition desirably can have a water content of from about 10% to about 20%, e.g., from about 12% to about 15%. The amount of enzyme(s) is suitably from about 0.0005% to about 0.0012%, such as at least about 5ppm.

Suitably the composition comprises from about 0.05 to about 2.0, such as from about 0.3 to about 1.0, optimally from about 0.4 to about 0.6 FTU/g of a phosphatase, e.g., a phytase. A xylanase can be present at from about 0.5 to about 50, e.g., from about 1 to about 40 EXU/g. Alternatively, or in addition, a cellulase can be present at from about 0.1 to about 1.0, e.g., from about 0.2 to about 0.4 BGU/g.

A fifth preferred aspect relates to a process for promoting the growth of an animal, the process comprising feeding an animal with a diet that comprises a granulate of the second aspect or a composition of the fourth aspect. Here, the animal diet can include either the granulate itself, or the granulate present in a feed.

A sixth preferred aspect of the present invention relates to the use of the granulate of the second preferred aspect in, or as a component of, an animal feed or for use in an animal diet.

A seventh preferred aspect of the present invention relates to the use of a composition comprising at least about 15% (w/w) of an edible carbohydrate polymer as a carrier for an enzyme to improve the pelleting stability of the enzyme.

Suitable animals include farm animals (e.g., pigs, poultry, livestock and the like), non-ruminants or monogastric animals (e.g., pigs, fowl, poultry, marine animals such as fish and the like), ruminants (e.g., bovine or ovine, such as cows, sheep, goats, deer, calves, lambs and the like). Poultry includes but is not limited to chickens, hens and turkeys.

Preferred features and characteristics of one aspect of the invention are equally applicable to another mutatis mutandis.

The following Examples are presented merely to illustrate the invention, and are not intended, or to be construed as, being limiting.

EXAMPLES

General Materials and Methods

Extrusion tests were performed using a Fuji Paudal DG-LL basket extruder, with screen openings of 1.0 mm, screen thickness 1.2 mm, operating speed of 70 rpm, and a current of 0.6–2.0 A.

The spheroniser was a Fuji Paudal Marumerizer QJ-400, with a charge volume of 3 litres, plate pitch of 3 mm, retention time of 45–200 seconds and rotating speed of 750 rpm.

The high shear granulation tests were conducted using a Lödige type high shear granulator FM20, with a chopper speed of 1500 rpm and a ploughshare speed of 1500 rpm. Powder was placed in the granulator and the enzyme-containing liquid was sprayed on top. The resulting granulates were dried in fluid bed drier.

The enzyme solutions used were:
an ultra-filtrate of an Aspergillus derived phytase with an activity of 16840 FTU/g, and a dry solids content of 22.4% (w/w) (Examples 1 to 7).
an ultra-filtrate containing a Trichoderma derived mixture of endo-xylanase and β-glucanase activities of 12680 EXU/g and BGU/g, and a dry solids content of 20.6% (w/w) (Example 8).

Phytase activity was determined according to the procedure "ISL-method 6169611" (manual vanadate assay). β-glucanase activity was determined according to the procedure "ISL-method 6217011" (manual viscosimetric assay). Endo-xylanase activity was determined according to the procedure "ISL-method 6216911" (manual viscosimetric assay). ISL-methods are obtainable on request from Gist-brocades, Food Specialties, Agri Ingredients Group, Wateringseweg 1, P.O. Box 1,2600 Mass., Delft, The Netherlands.

EXAMPLE 1

Preparation of corn starch-based enzyme granulate by kneading, extrusion, spheronisation and drying An enzyme preparation was obtained by mixing and kneading a mixture of 60% (w/w) of corn starch with 40% (w/w) of an ultra-filtrate containing phytase. This mixture was extruded using the Fuji Paudal basket extruder to obtain a wet extrudate which was then spheronised in the MARUMERISER™ for one minute to obtain round particles of an average diameter of 780 μm. These particles were subsequently dried in a fluid bed drier for 20 minutes at a bed temperature of 40° C., and an inlet temperature of 75° C. Approximately 500 kg of the granules were dried in 18 minutes. The thus obtained dry enzyme granulate had an activity of 6980 FTU/g.

EXAMPLE 2

Preparation of a corn starch-based enzyme granulate by high shear granulation and drying The phytase ultra-filtrate and corn starch were mixed in a batch type high shear granulator of the Lödige type, with a batch size of 20 litres. The granulator was filled with 60% (w/w) of corn starch and 40% (w/w) ultra-filtrate was sprayed into the mixer during the mixing process. After addition of the ultra-filtrate (10 minutes) the granulator continued mixing for another 5 minutes to allow the particles to be formed and compacted. The thus obtained granules were dried in a fluid bed drier as in Example 1. The resulting granulate had an activity of 7420 FTU/g. The median diameter of the particles was 480 μm.

EXAMPLE 3

Preparation of a corn starch-based enzyme granulate by mixing, pelleting and drying A mixture of 40% (w/w) of the phytase ultra-filtrate and 60% (w/w) of corn starch was prepared. The mixture was pelleted using a Schlütter Press type PP85, where the extrudates were cut off by rotating knives at the extruder head, with a die plate containing holes of 1 mm in diameter. The pellets were dried as in Example 1, resulting in a final product with an activity of 7460 FTU/g. The median diameter of the particles was 1080 μm.

EXAMPLE 4

Preparation of a potato starch-based enzyme granulate containing soy oil and $MgSO_4$ additions by mixing, kneading, pelleting and drying In a mixer/kneader 30 kg of potato starch was added and 2.5 kg of Soy oil was mixed in. Subsequently the phytase ultra-filtrate was added containing $MgSO_4.7H_2O$— (3.5 kg of $MgSO_4 \cdot 7H_2O$ was dissolved in 14 kg of ultra-filtrate). The product was mixed thoroughly in the kneader, then extruded and dried in a fluid bed drier as in Example 1. This resulted in a product of 5870 FTU/g.

EXAMPLE 5

Preparation of a rice starch-based enzyme granulate by mixing, kneading, extrusion, spheronisation and drying A mixture was prepared by mixing and kneading 62% (w/w) rice starch and 38% (w/w) of the phytase ultra-filtrate. This mixture was extruded using the Fuji Paudal basket extruder to obtain a wet extrudate which was then spheronised in the MARUMERISER™ for one minute to obtain round particles of an average diameter of 785 μm. These particles were subsequently dried in a fluid bed drier as in Example 1. The final activity of the granulate was 7280 FTU/g.

EXAMPLE 6

Preparation of a corn starch-based enzyme granulate containing an HPMC addition by mixing, kneading, extrusion, spheronisation and drying An enzyme preparation was obtained by kneading a mixture of 54% (w/w) of corn starch, 5% of HPMC (hydroxy-propyl-methyl-cellulose) and 41% (w/w) of a phytase ultra-filtrate. This mixture was extruded using the Fuji Paudal basket extruder to obtain a wet extrudate which was spheronised in the MARUMERISER™ for one minute to obtain round particles of an average diameter of 780 gm. These were subsequently dried in a fluid bed drier for 20 minutes at 40° C. bed temperature, and 75° C. inlet temperature. The thus obtained dry enzyme granulate had an activity of 8470 FTU/g.

EXAMPLE 7

Preparation of a corn starch-based enzyme granulate containing an HEC addition by mixing, kneading, extrusion, spheronisation and drying An enzyme preparation was obtained by mixing and kneading 54% (w/w) of corn starch, 5% (w/w) of HEC (hydroxy-ethyl-cellulose) with 41% (w/w) of the phytase ultra-filtrate. This mixture was extruded using the Fuji Paudal basket extruder to obtain a wet extrudate which was spheronised in the MARUMERISER™ for one minute to obtain round particles of an average diameter of 780 µm. These were subsequently dried in a fluid bed drier for 20 minutes at 40° C. bed temperature, and 75° C. inlet temperature. The thus obtained dry enzyme granulate had an activity of 8410 FTU/g.

EXAMPLE 8

Preparation of a corn starch-based enzyme granulate by high shear granulation and drying In a batch type high shear granulator of the Lödige type, with a batch size of 20 litres, 60% (w/w) of corn starch was mixed with 40% (w/w) of the ultra-filtrate containing endo-xylanase and β-glucanase in the following manner. The granulator was filled with corn starch and the ultra-filtrate was sprayed into the mixer during the mixing process. After addition of the ultra-filtrate (10 minutes) the granulator was operated for another 5 minutes to allow the particles to be formed and compacted. The thus obtained granules were dried in a fluid bed drier as in Example 1. The resulting granulate had an activity of 13100 EXU/g and 5360 BGU/g.

EXAMPLE 9

Comparison of the pelleting stabilities

The different enzyme granulates of the invention were subjected to a pelleting trial and their pelleting stability was compared with those of the standard feed enzyme formulations. The pelleting trial consisted of mixing the enzyme (granulate) with a feed premix at 1000 ppm. This mixture was treated by injection of steam to give a temperature rise to 70° C., after which the mixture was pelleted in a pelleting machine to obtain the feed pellets, which were subsequently dried. This type of process is typical for the feed industry to obtain feed pellets.

For NATUPHOS™, a phytase containing formulation used as a standard, for comparison, was a mixture of wheat middlings with spray dried ultra-filtrate.

For NATUGRAIN™, an enzyme preparation containing β-glucanase and endo-xylanase, this is a fluid bed prepared granule, made by coating a salt core with an enzyme layer, applied by spraying the core with an ultra-filtrate.

Table 1 summarizes the results of the pelleting trials. It is apparent from Table 1 that the granulates made using a carbohydrate carrier gave improved pelleting yields when compared with standard formulations.

TABLE 1

Results of the pelleting tests

| Example Number | Enzyme activity of the granules FTU/g | EXU/g BGU/g | Enzyme yield after pelleting at 70° C. % |
|---|---|---|---|
| Ex. 1 | 6980 | — | 54.9 |
| Ex. 2 | 7420 | — | 51.8 |
| Ex. 3 | 7460 | — | 62.8 |
| Ex. 4 | 5870 | — | 62.7 |
| Ex. 5 | 7280 | — | 54.7 |
| Ex. 6 | 8470 | — | 69.6 |
| Ex. 7 | 8410 | — | 67.3 |
| Ex. 8 | — | 13100 | 61.3 |
|  |  | 5360 | 25.8 |
| Standard NATUPHOS ™ | 5250 | — | 29.8 |
| Standard NATUGRAIN ™ | — | 8150 | 38.6 |
|  |  | 6030 | 10.4 |

It is clear from Table 1 that the type of granulation method, i.e., mechanical processing, is not critical to addressing the problems to be solved by the invention. Formulations using the carbohydrate polymer provided a much better pelleting stability as compared to the known NATUPHOS™ and NATUGRAIN™ formulations.

All the references cited herein, including patents, patent applications, and publications, are hereby incorporated in their entireties by reference.

What is claimed is:

1. A process for the preparation of an enzyme-containing granulate suitable for use in an animal feed, the process comprising:
   (a) making a mixture of (1) an enzyme, (2) a solid carrier comprising at least about 15% (w/w) of an edible carbohydrate polymer that has less than 5% (w/w) protein, and (3) water
   (b) mechanically processing the mixture from (a) by low pressure extrusion such that extrusion does not allow temperature of the mixture to rise above 40° C. to obtain enzyme-containing granules; and
   (c) drying the enzyme-containing granules obtained in (b).

2. A process according to claim 1 wherein the water and enzyme are provided as an enzyme-containing aqueous liquid.

3. A process according to claim 2 wherein the liquid is a filtrate derived from a fermentation process resulting in production of the enzyme.

4. A process according to claim 1 wherein the enzyme-containing granules from (b) are subject to spheronising and/or the drying of (c) is in a fluid bed agglomerator.

5. A process according to claim 1 wherein the mixture of (a) is kneaded before extrusion.

6. A process according to claim 1 wherein the granules obtained are spheronised prior to drying.

7. Enzyme-containing granules produced by a process according to claim 1.

8. Enzyme-containing granules according to claim 7 wherein the granules comprise one at least one divalent cation.

9. Enzyme-containing granules according to claim 7 wherein the granules comprise one or more hydrophobic, gel-forming or water insoluble compound(s).

10. Enzyme-containing granules according to claim 9 wherein the hydrophobic, gel-forming or water insoluble compound comprises a component selected from the group consisting of cellulose, polyvinyl alcohol (PVA), and an edible oil.

11. Enzyme-containing granules according to claim 10 wherein: (a) the cellulose is derivatised and is selected from the group consisting of hydroxy-propyl-methyl-cellulose, carboxy-methyl-cellulose and hydroxy-ethyl-cellulose; or (b) the edible oil is soy oil or canola oil; or (c) the derivatised cellulose and hydroxy-ethyl-cellulose, and the edible oil is soy oil or canola oil.

12. Enzyme-containing granules according to claim 7 wherein the enzyme is selected from the group consisting of a phytase, endo-xylanase, and a β-glucanase.

13. A composition comprising enzyme-containing granules according to claim 7.

14. A composition according to claim 13 which is an edible feed composition.

15. A composition to claim 13 which is an animal feed.

16. A composition which comprises pellets of one or more feed substance(s) or ingredient(s) for making a feed substance enzyme-containing granules according to claim 7.

17. A composition according to claim 16 wherein the ratio of enzyme-containing granules feed substance(s) or ingredients for making a feed substance is at least about 1 g: 1 kilogram.

18. A process for promoting the growth of an animal, the process comprising feeding an animal with a diet that comprises a composition according to claim 13.

19. A process for the preparation of an animal feed or a premix for making an animal feed, the process comprising mixing enzyme-containing granules according to claim 7 with one more animal feed substance(s) or ingredient(s) for making an animal substance.

20. A process according to claim 19 wherein the mixture of feed substance(s) and enzyme-containing granules is sterilised or treated with steam, and is pelletised.

21. A process according to claim 20 wherein after pelletisation the mixture is dried.

22. A composition which is an animal feed or a premix for making an animal feed prepared by a process according to claim 19.

23. A process for promoting the growth of an animal, wherein said process comprises feeding said animal with enzyme-containing granules according to claim 7 or a composition according to claim 22.

* * * * *